United States Patent [19]

Watkins

[11] Patent Number: 4,826,812
[45] Date of Patent: May 2, 1989

[54] ANTIGLAUCOMA AGENT

[75] Inventor: Robert W. Watkins, Great Meadows, N.J.

[73] Assignee: Schering Corporation, Kenilworth, N.J.

[21] Appl. No.: 889,436

[22] Filed: Jul. 23, 1986

Related U.S. Application Data

[60] Continuation-in-part of Ser. No. 840,526, Mar. 13, 1986, abandoned, which is a continuation of Ser. No. 703,242, Feb. 20, 1985, abandoned, which is a division of Ser. No. 662,853, Oct. 19, 1984, abandoned, which is a continuation of Ser. No. 453,257, Dec. 27, 1982, abandoned.

[51] Int. Cl.$^4$ ............... A61K 37/00; A61K 31/40
[52] U.S. Cl. ............................ 514/19; 514/409; 514/913
[58] Field of Search ............... 514/409, 913, 16, 19; 548/409

[56] References Cited

U.S. PATENT DOCUMENTS

| | | | |
|---|---|---|---|
| 4,046,889 | 9/1977 | Ondetti et al. | 424/274 |
| 4,156,010 | 5/1979 | Hirachmann | 424/278 |
| 4,168,267 | 9/1979 | Petrillo | 424/274 |
| 4,179,517 | 12/1979 | Mechoulam et al. | 424/283 |
| 4,197,301 | 4/1980 | Smith et al. | 424/251 |
| 4,226,775 | 10/1980 | McEloy et al. | 424/274 |
| 4,311,697 | 1/1982 | Krapcho | 548/409 |
| 4,316,905 | 2/1982 | Krapcho | 424/274 |
| 4,325,945 | 4/1982 | Natarajan et al. | 548/409 |
| 4,442,089 | 4/1984 | Horovitz | 514/19 |
| 4,470,972 | 9/1984 | Gold et al. | 514/19 |

FOREIGN PATENT DOCUMENTS

| | | |
|---|---|---|
| 12401 | 10/1979 | European Pat. Off. . |
| 0050800 | 5/1982 | European Pat. Off. . |
| 0099239 | 1/1984 | European Pat. Off. . |

OTHER PUBLICATIONS

Chemical Abstracts, vol. 88, No. 7, 1978, p. 313, No. 47944f.
Chemical Abstracts, vol. 92, No. 25, 1980, p. 368, No. 212468h.
Chemical Abstracts, vol. 95, Nos. 13, 21, 1981, pp. 421, 453 Nos. 112364q, 185021k.
Chemical Abstracts, vol. 97, No. 13, 1982, p. 122, No. 104746s.
Chemical Abstracts, vol. 99, No. 21, 1983, p. 421, No. 173430n.
Klin. Mbl. Augenheilk 162 (1973), 637–642.
Biol. Abst. 71, 34826, 47987.
Biol. Abst. 72, 35,289.

Primary Examiner—Douglas W. Robinson
Attorney, Agent, or Firm—Joseph T. Majka; Stephen I. Miller

[57] ABSTRACT

A method for reducing intraocular pressure by topically applying 7-{N-[1(S)-Carboxy-3-phenylpropyl]-(S)-alanyl}-1,4-dithia-7-azaspiro[4.4]nonane-8(S)-carboxylic acid is disclosed.

4 Claims, No Drawings

ANTIGLAUCOMA AGENT

CROSS REFERENCE TO RELATED APPLICATION

This application is a continuation-in-part of application Ser. No. 840,526 filed Mar.13, 1986 (now abandoned) which was a continuation of application Ser. No. 703,242 filed Feb. 20, 1985 (now abandoned) which was a divisional of application Ser. No. 662,853 filed Oct. 19, 1984 (now abandoned) which was a continuation of application Ser. No. 453,257 filed Dec. 27, 1982 (now abandoned).

BACKGROUND OF THE INVENTION

Glaucoma is an ocular disease complex associated with an elevated pressure within the eye (i.e., intraocular pressure, IOP). As a result of the elevated IOP, damage to the optic nerve head resulting in irreversible loss of visual function ray ensue. Untreated, this condition may eventually lead to blindness.

Ocular hypertension, i.e., the condition of elevated intraocular pressure without optic nerve head damage or characteristic glaucomatous visual field loss, is now believed by the majority of ophthalmologists to represent the earliest phase in the onset of glaucoma.

A number of the drugs presently employed to treat glaucoma are not entirely satisfactory, particularly in the earliest course of the disease when the side effects they produce are often worse than the symptoms of the disease.

Epinephrine used as a topical solution, must be utilized cautiously in patients with high blood pressure, diabetes, hyperthyroidism and cerebral artereosclerosis due to the possibility of systemic action.

Timolol, a clinically utilized, topically applied agent for lowering intraocular pressure, must be used with caution in patients in whom beta-adrenergic blockade may be undesirable. Systemic absorption of topically administered timolol and systemic beta-blockade are responsible for the contraindication of timolol therapy for gluacoma in patients with compromised pulmonary function.

Pilocarpine, a topical drug, although considered systemically harmless and quite effective, may cause considerable local difficulties. Pupil constriction may cause the eye to lose its ability to adapt from light to dark. Accomodation may become stimulated so that the patient's refraction is sometimes incorrect and vision becomes blurred. The drug itself may cause a local vasodilation and red eyes. Irritation is common.

Carbonic anhydrase inhibitors have been used systemically but they have a number of disadvantages. While effective in lowering intraocular pressure, they often cause a numbness and tingling, gastrointestinal upsets and, frequently, depression, lethargy, a loss of appetite, and general malaise. European Patent Application No. 81400326.5, Publication No. 36,351 attempts to overcome these difficulties by the topical administration of an alkali metal salt of a carbonic anhydrase inhibitor.

The present invention provides a new method for reducing and controlling the elevated intraocular pressure associated with glaucoma.

SUMMARY OF THE INVENTION

The invention sought to be patented in its pharmaceutical composition aspect is a topical ophthalmologically acceptable composition useful for reducing and controlling the elevated intraocular pressure associated with glaucoma which comprises an intraocular pressure reducing effective amount of 7-{N[1(S)-Carboxy-3-phenylpropyl]-(S)-alanyl}-1,4-dithia-7azaspiro[4.4]nonane-8(S)-carboxylic acid, compound I, in combination with an ophthalmologically acceptable carrier for topical use.

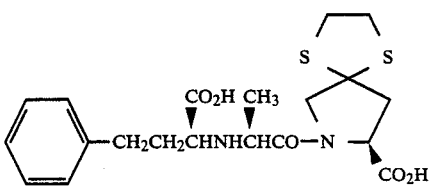

In the above formula I the heavy line (━━) utilized at the chiral centers means that the substituent so bonded is projected above the plane of the paper. The configuration at these chiral centers is denoted as "S".

The invention sought to be patented in its pharmaceutical method aspect is a method for reducing and controlling the elevated intraocular pressure associated with glaucoma in a human or other mammal which method comprises administering to said human an intraocular pressure lowering effective amount of the above-defined pharmaceutical composition.

DESCRIPTION OF THE INVENTION

Compound I utilized in the topical ophthalmologically acceptable pharmaceutical composition and method of the invention is known in the art and may be readily prepared by methods known in the art of synthetic organic chemistry, see for example U.S. Pat. No. 4,470,972 examples 2 and 6.

The utility described for Compound I in said patent is the inhibition of angiotensin converting enzyme (ACE). Other ACE inhibitors are known in the art, and may have a variety of structures. See, for example, An. Rev. Biochem., 51, 283(1982) and references cited therein.

U.S. Pat. No. 4,442,089 broadly teaches the generic concept that glaucoma may be treated both topically and systemically by the administration of ACE inhibitors. Compound I of the instant invention is not specifically disclosed in or described by the reference. In *Preventive Medicine*, v.8, no. 2, p. 146 (1979) it is disclosed that the ACE inhibitor D-2-methyl-3-mercaptopropanoyl-L-proline (captopril) lowers intraocular pressure when administered systemically to renal hypertensive dogs.

In the applicant's opinion, the closest structurally related compound to instant Compound I which is disclosed in U.S. Pat. No. 4,442,089 is 1-[N-[(S)-1carboxy-3-phenylpropyl]-L-alanyl]-L-proline, 1'-ethyl ester (II, R=ethyl).

An even more closely structurally related compound to instant compound I, i.e. compound III (compound III is compound II wherein R=hydrogen) also known to possess ACE inhibitory properties was directly compared against compound I in the test procedure described below. Results from this test demonstrate that in terms of the minimal effective concentration (i.e., topical concentration causing a significant lowering of IOP lasting at least 3 hours) compound I is 1 order of magnitude more potent as an ocular hypotensive agent than is compound III. In addition, compound I produced reductions in intraocular pressure that lasted nearly three times longer than those produced by compound III when each was administered at the same concentration. These results could not have been predicted based merely upon the observed structural similarities of compounds I and III, or from their known ACE inhibitory potencies.

When topically administered to the eye, the compound of the invention reduces intraocular pressure (IOP). For example, compound I (0.001-1.0%) caused falls in IOP of a magnitude at least comparable to the reductions in IOP produced by the anti-glaucoma agent timolol (0.25-2.0%) when tested by the following procedure:

TEST PROCEDURE

Male New Zealand white rabbits having a normal IOP were conditioned to the laboratory setting for at least one 4 hr period before being used to study drug effects. A Makay-Marg applanation tonometer was used to measure IOP and readings, in mm Hg, were taken in triplicate and the average recorded as described in Watkins et al., J. Ocular Pharmacol., 1, 161 (1985).

The left lower eyelid was retracted to form a pouch and 1 drop of a local anesthetic was irrigated over the cornea. The lower eyelid was then held closed over the eye for about 1 min. Corneal anesthesia was repeated before each set of IOP determinations. Readings were taken just before dosing with drug (0 time) and at hourly intervals thereafter. Drugs were administered in a 50 ul volume in the same manner as the anesthetic.

The compound of the invention may be administered in the form of ophthalmic pharmaceutical compositions adapted for topical administration to the eye; such as solutions, suspensions, ointments and solid inserts. Formulations of this compound may contain from 0.001 to 2.5% and especially 0.1% to 1% of medicament. Other concentrations may be employed provided the dose is effective in lowering intraocular pressure. As a unit dosage form, between 0.05 to 1.25 mg., preferably 0.025 to 1.25 mg., and especially, 0.05 to 0.5 mg. of the active compound is applied to the human eye, generally on a daily basis. Individual dosage requirements are variable; however, and must be administered on the basis of the severity of the disease and the response of the patient.

To prepare suitable dosage forms, compound I may be conveniently admixed with a non-toxic pharmaceutically acceptable carrier suitable for topical ophthalmolgic administration. Typical of such pharmaceutically acceptable carriers are, for example, water, mixtures of water and water miscible solvents such as lower alkanols or vegetable oils, petroleum based jelly, and including also from 0.5 to 5% by weight of hyroxyethyl cellulose, ethyl oleate, carboxymethyl cellulose, polyvinylpyrrolidone, and other water soluble ophthalmologically acceptable non-toxic polymers, for example, cellulose derivatives such as methyl cellulose, alkali metal carboxymethyl cellulose, hydroxyethyl, cellulose, hydroxypropyl cellulose, hydroxypropylmethyl cellulose; acrylates such as polyacrylic acids salts, ethylacrylates; polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum and mixtures of these polymers. The pharmaceutical preparation may also contain non-toxic auxiliary substances such as emulsifying, preserving, wetting, bodying agents and the like, as for example, polyethylene glycols 200, 300, 400 and 600, carbowaxes 1,000, 1,500, 4,000, 6,000 and 10,000, antibacterial components such as quaternary ammonium compounds; phenylmercuric salts known to have cold sterilizing properties and which are non-injurious in use; thimerosal, methyl and propyl paraben, benzyl alcohol, phenyl ethanol; buffering ingredients such as alkali metal chloride, borate, acetate, gluconate buffers; antioxidants such as sodium metabisulfite, butylated hydroxyanisole (BHA), butylated hydroxytoluene (BHT) and the like; and other conventional ingredients such as sorbitan monolaurate, triethanolamine, oleate, polyoxyethylene sorbitan monopalmitylate, dioctyl alkali metal sulfosuccinate, monothioglycerol, ethylenediamine tetracetic acid and the like.

Additionally, suitable ophthalmic vehicles can be used as carrier media for the present purpose including conventional phosphate buffer vehicle systems, isotonic boric acid vehicles, isotonic alkali chloride vehicles, tris and the like.

The pharmaceutical preparation may also be in the form of a solid insert. For example, one may use a solid water soluble polymer as the carrier for the medicament. Inserts that are known in the art that are suitable for this use include those described in British patent No. 15611, and in U.S. Pat. Nos. 3,993,071; 3,986,510; 3,868,445; and 3,867,510. Solid water insoluble inserts, such as those prepared from ethylene vinyl acetate copolymer, may also be utilized.

The compositions of the invention may include additional therapeutic agents in addition to Compound I. For example antibiotics, anesthetics as well as other IOP lowering agents may be present.

Where utilized herein, the term "controlling the elevated intraocular pressure" means the regulation, attenuation and modulation of increased intraocular tension, which is the primary diagnostic manifestation of the disease glaucoma. The term also means that the diminution, in the otherwise elevated intraocular pressure, obtained by the practice of the invention is maintained for a significant period of time as, for example, between consecutive doses of the composition of the invention.

I claim:

1. A topical ophthalmologically acceptable composition useful for reducing elevated intraocular pressure which comprises an intraocular pressure reducing effective amount of 7-{-[1-(S)-carboxy-3-phenylpropyl]-(S)-alanyl}-1,4-dithia-7-azaspiro[4.4]nonane-8(S)-carboxylic acid in combination with an ophthalmologically acceptable carrier containing an acetate or phosphate buffer in an isotonic alkali chloride vehicle for topical use.

2. The composition defined in claim 1 wherein 7-{N-[1(S)-carboxy-3-phenylpropyl]-(S)-alanyl}-1,4-dithia-7-azaspiro[4.4]nonane-8(S)-carboxylic acid is present in a concentration from between 0.1% to 2.5%.

3. A method for reducing elevated intraocular pressure which comprises topically adminstering a composition comprising an intraocular pressure reducing effective amount of 7-{N-[1(S)-carboxy-3-phenylpropyl]-(S)-alanyl}-1,4-dithia-7-azaspiro[4.4]nonane-8(S)-carboxylic acid in combination with an ophthalmologically acceptable carrier for topical use.

4. The method defined in claim 3 wherein said 7-{N-[1(S)-carboxy-3-phenylpropyl]-(S)-alanyl}-1,4-dithia-7-azaspiro[4.4]nonane-8(S)-carboxylic acid is present in said composition in a concentration from between 0.1% to 2.5%.

* * * * *